(12) United States Patent
Duncan et al.

(10) Patent No.: US 8,862,485 B2
(45) Date of Patent: Oct. 14, 2014

(54) SYSTEM AND METHOD FOR DATA QUALITY ASSURANCE CYCLE

(75) Inventors: Brenna Duncan, San Diego, CA (US); Hui-Wen Harrison, San Diego, CA (US); Bruce Russell, San Diego, CA (US); Vani Bobba, San Diego, CA (US)

(73) Assignee: Rady Children's Hospital—San Diego, San Diego, CA (US)

( * ) Notice: Subject to any disclaimer, the term of this patent is extended or adjusted under 35 U.S.C. 154(b) by 783 days.

(21) Appl. No.: 12/252,256

(22) Filed: Oct. 15, 2008

(65) Prior Publication Data

US 2010/0094836 A1     Apr. 15, 2010

(51) Int. Cl.
*G06Q 50/24* (2012.01)
*G06Q 30/04* (2012.01)

(52) U.S. Cl.
CPC ...................................... *G06Q 30/04* (2013.01)
USPC ................................ 705/3; 707/803; 707/736

(58) Field of Classification Search
USPC ....................................... 707/736, 803; 705/3
See application file for complete search history.

(56) References Cited

U.S. PATENT DOCUMENTS

| | | | | |
|---|---|---|---|---|
| 5,235,702 A | * | 8/1993 | Miller | 1/1 |
| 7,376,573 B1 | * | 5/2008 | Costonis et al. | 705/4 |
| 2005/0027567 A1 | * | 2/2005 | Taha | 705/2 |
| 2005/0075544 A1 | * | 4/2005 | Shapiro et al. | 600/300 |
| 2005/0209893 A1 | * | 9/2005 | Nahra et al. | 705/4 |
| 2006/0122865 A1 | * | 6/2006 | Preiss et al. | 705/2 |
| 2006/0293925 A1 | * | 12/2006 | Flom | 705/3 |
| 2007/0288268 A1 | * | 12/2007 | Weeks | 705/3 |
| 2008/0097789 A1 | * | 4/2008 | Huffer | 705/2 |
| 2008/0147436 A1 | * | 6/2008 | Ohlsson | 705/2 |
| 2008/0201172 A1 | * | 8/2008 | McNamar | 705/3 |
| 2008/0319942 A1 | * | 12/2008 | Courdy et al. | 707/3 |
| 2009/0138289 A1 | * | 5/2009 | Klass et al. | 705/3 |

\* cited by examiner

*Primary Examiner* — Cam-Y Truong
(74) *Attorney, Agent, or Firm* — Pattric J. Rawlins; Procopio, Cory Hargreaves & Savitch LLP

(57) ABSTRACT

A system and method for automated quality assurance including a quality assurance application server for managing quality assurance. The quality assurance application server includes an application configuration module which has a data configuration module configured to define configurable reference fields to be captured and reviewed during the processing of the records. The application configuration module also has a rules configuration module to receive, create or modify a set of rules where the configurable reference fields are selectable when the rules are defined. The system also includes a portal module for processing the received records and applying the set of rules to the record. The portal module includes a quality assurance records review module configured to evaluate and validate the received records and to generate an output utilized to validate the record to ensure compliance with a data recipient, for example payer billing, standards.

29 Claims, 19 Drawing Sheets

SYSTEM AND METHOD FOR DATA QUALITY ASSURANCE CYCLE

BACKGROUND

1. Field of the Invention

The present invention generally relates to data processing systems, and more particularly relates to systems and methods for providing quality assurance in data processing cycles.

2. Related Art

A conventional data processing cycle involves a considerable amount of manual intervention. For example, the revenue cycle involves a considerable amount of manual billing and is very labor intensive and therefore costly and also significantly more prone to human error. Incorrect data are entered during the conventional data processing cycle due to human errors (e.g. typo), lack of knowledge (e.g. data entry person did not realize that the data entered would violate clause in the contract), and other reasons. These data error will cost more time, money and human resources if the errors are not corrected before being transmitted to the data recipient (could be a person or a system). In the healthcare revenue cycle the manifestation would be a claim denied by a payer, which results in rework on the claim by the hospital's billing department, re-transmission of the claim and review of the reworked claim by the payer before the hospital can receive the reimbursement from the payer. The delay in collection period, the time it took to deny a claim, request for rebill, and review the reworked claim cost both the data sender and the data recipient more time and money to complete the data processing.

These significant problems with the conventional data processing cycle have created a need in the industry for improved systems and methods that overcome the problems described above.

SUMMARY

Described herein are systems and methods that provide for automated quality assurance in the data processing cycle that promotes compliance with data recipient's requirements and thereby reduces rejection, loss of profit or need for rework after data is transmitted. In one embodiment a system and method for automated quality assurance in the data processing cycle is provided. The system includes a first user interface that is configured to receive data or records, of a patient for example, that can be utilized to generate a completed record, a claim for a billing for example. The received records/data are populated in a storage area. A quality assurance application server is used for managing quality assurance processing including validating the format and content of the data/records that can be used to create a completed record, for example a claim or a bill in the context of the healthcare revenue cycle. The quality assurance application server includes an application configuration module which includes a data configuration module configured to define configurable reference fields to be captured and reviewed during the processing of the records/data. The application configuration module has a rules configuration module to create or modify a set of rules where the configurable reference fields are selectable when the rules are defined. The application configuration module contains two modules to control layout and placement of the configurable reference fields for display to the user. A forms configuration module to arrange the configurable portion of the user interface and a reports module to arrange standard report layouts. The application configuration module has an import configuration module to adapt external data sources to assist in the transport of raw data into the system. The application configuration module has an integration system configuration module 50 to configure links to external reference systems (for example, a document imaging system). These links allow the user to jump to another system interface from within the system. The system includes a portal module that provides the user interface for a user to review records received and for processing the received records and applying the set of rules to the records. The portal module includes a quality assurance records review module configured to evaluate and validate the received records and to generate an output utilized to validate the data/records to ensure compliance with data recipient standards, for example. Users can make corrections directly into the point of service (POS) host system. The portal module includes a quality assurance review audit module that allows users to validate the accuracy of the records received. This user interface allows a user to review records assigned to them from a pool of records within a workflow queue. Each workflow queue, for example, can include a list of records that need to be reviewed. Records can pass from one queue to another based on a configurable amount of time or when the reviewer is done working with that record. For example, records can be placed in a data entry queue that is marked as read only allowing the originator to see errors that occur and to correct them until they pass to the next queue after a predetermined period of time, for example. The next queue can be a review queue where a reviewer can add and remove errors and comments. The reviewer can make corrections to the data in the host system. In one embodiment, the records pass through an audit workflow queue where an auditor type user can review the work done on the record as it passed through the previous workflow queues. Auditing can occur after the review queue. The portal module can include a records management module that allows a user to assign and transfer records to other users using a configurable set of assignment rules. The assignment rules can be created, modified, and individually selected in order to assign records accurately to the user reviewing records within a workflow queue. The portal module contains a user management module. The user management module allows a user with the proper permissions to add, modify, and delete users. Jobs and roles can also be assigned to the user. These assignments grant or deny access to operations within the application to the defined user. Distribution groups can also be defined for delivery of reports and email notifications.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for automated quality assurance in a data processing cycle such as commercial billing systems found in the healthcare revenue cycle. The described systems and methods are implemented to ensure compliance with data recipient requirements. After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figure 1:
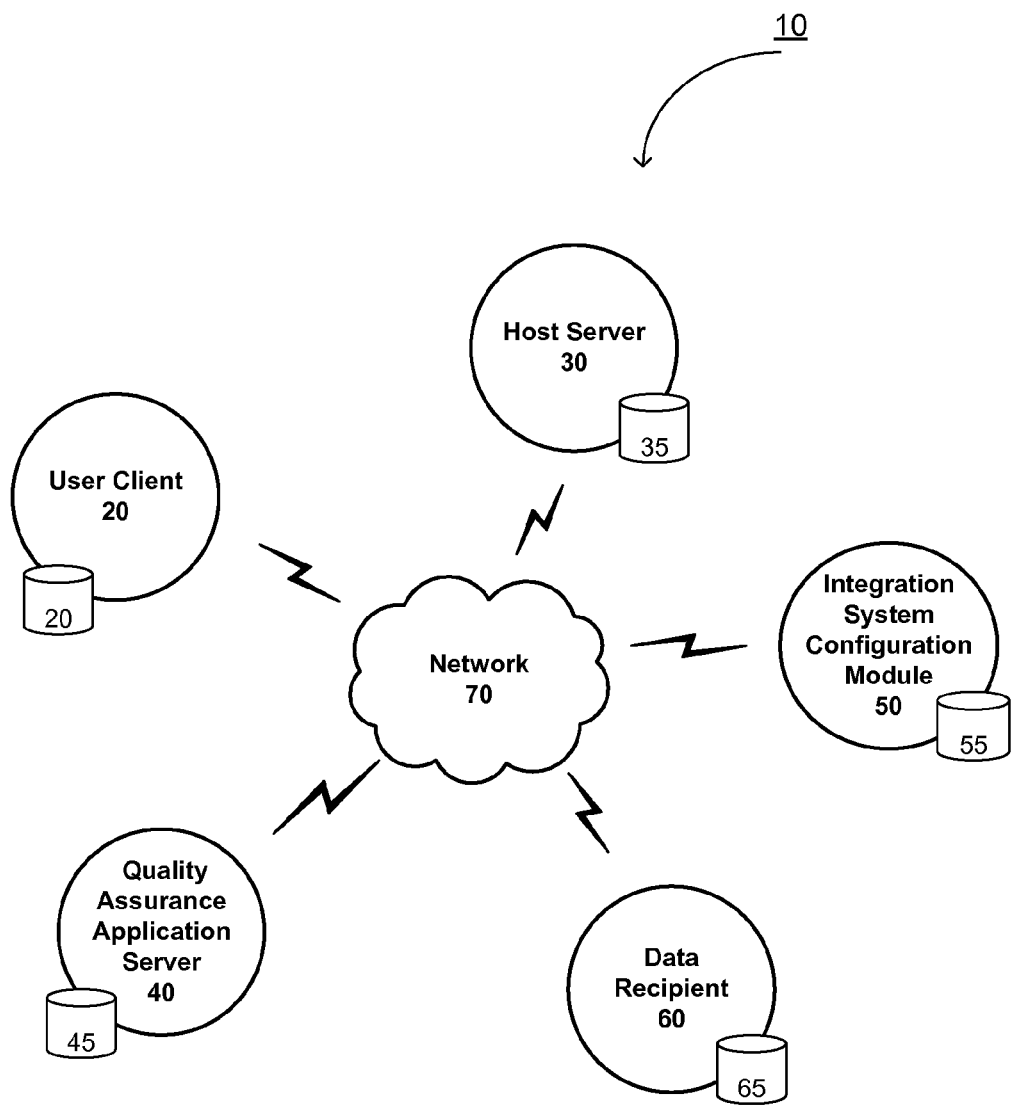
FIG. 1 is a network diagram illustrating an example data processing system for processing quality assurance records according to an embodiment of the present invention.

FIG. 1 is a network diagrams illustrating an example of data processing system for processing quality assurance records according to an embodiment of the present invention. In the illustrated embodiment, the system 10 comprises a user/client 20 (e.g., point of service data entry or a user interface), a host server 30 (e.g., a Hospital Information System ("HIS") server), quality assurance application server 40, integration system configuration module 50 (to link the quality assurance application server 40 to external systems e.g., insurance eligibility verification, document imaging), and the Data Recipient Systems 60 (e.g., insurance companies). The integration system configuration module 50 can be internal or external to the quality assurance application server. Each of these elements 20-60 are configured with a data storage area 25-65, respectively and are also communicatively coupled with one or more of the other components of the system 10 via a communication network 70 that may include wired and wireless, public and private, voice and data, and other types of communication networks including that particularly notorious combination of networks known as the Internet.

Figure 2:
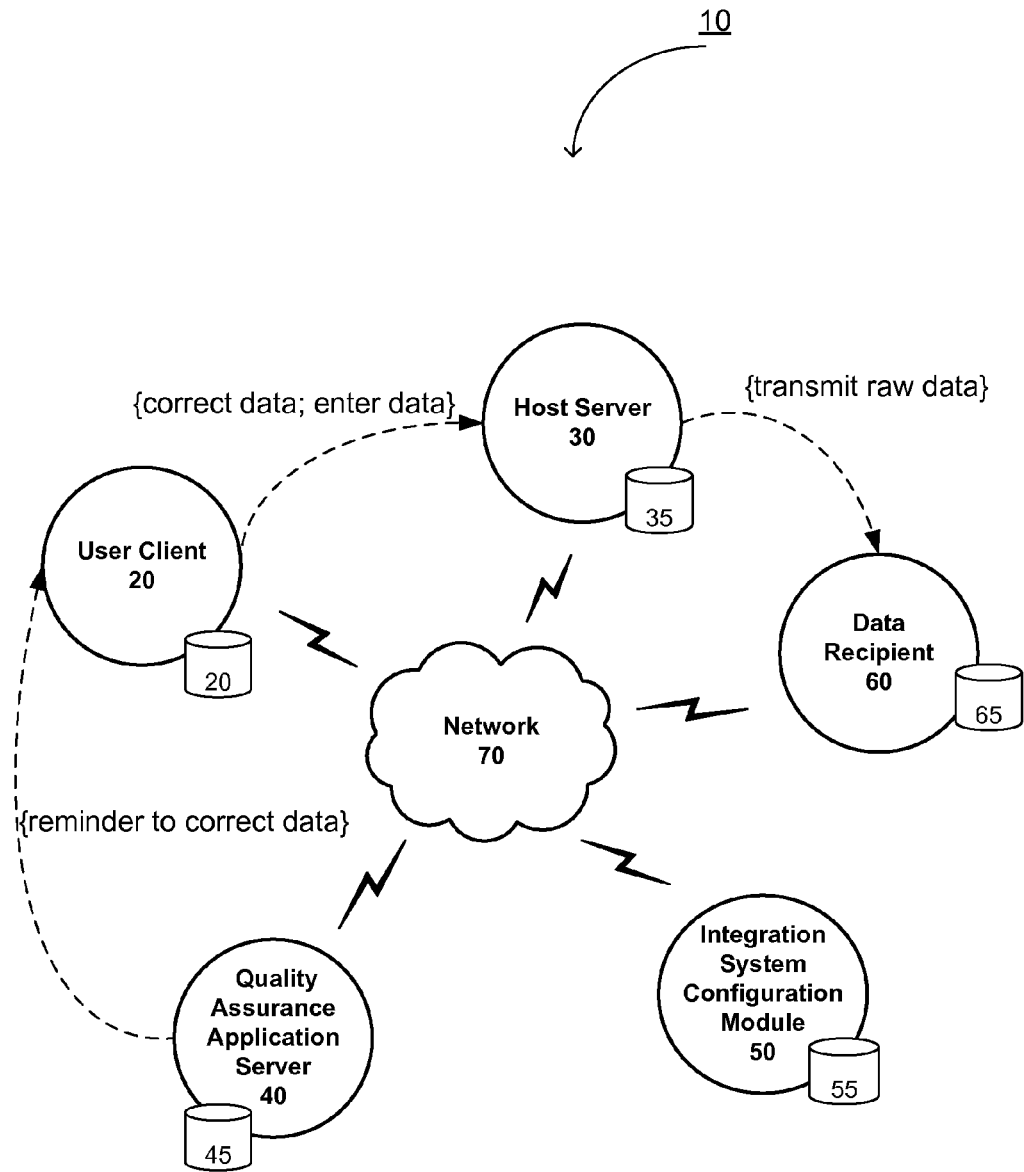
FIG. 2 is another network diagram illustrating an example data processing system operation for processing quality assurance records according to an embodiment of the present invention.

FIG. 2 illustrates a data processing cycle that can be implemented on the data processing system of FIG. 1. A user can change certain parameters while they are working with the application. These changes can be made in a user interface associated with the system. For example, column width or the order of the columns within the record display grid. These parameters can be saved by user and used in future sessions so that the user does not have to reset them each time. There are several roles a user can have assigned to them. Each role allows the user to access certain functions within the application. In some embodiments the users functions can be automated. Example roles of a user are described in Table 1 below.

TABLE 1

| Role | Functions |
| --- | --- |
| Data Entry | User is allowed to view data/records created by themselves to understand what can be corrected and how the data can be input better. |
| Reviewer | User is allowed to perform the duties of a quality assurance reviewer. This includes tasks such as viewing records, applying rules, managing errors and flags, transferring assigned records. |
| Review Supervisor | Same duties as the Reviewer plus the authority to manage other users work. |
| Auditor | User is allowed to perform duties of the QA Auditor. This includes tasks such as reviewing records processed by reviewers, overriding actions performed by reviewers, viewing statistics |
| Report Viewer | User can receive reports containing data for the application. This permission can be assigned to someone outside the application that only views reports. |
| Administrator | User is allowed to manage and configure the application. |

Data or records including registration information can be entered in the system via a user interface or a point of service device (i.e. user/client 20). The data or records can be processed through the data processing cycle and ultimately passed to the data recipient system 60, for example billing or payer system, as a complete record. There may be multiple different data recipient systems 60, which adds complexity to the data processing cycle because each data recipient system 60 may have a different format for the complete record and also different requirements for the content of a record. For example, in the healthcare revenue cycle, different payers have different format and data requirements for healthcare claims. Records that are created in the host system 30 are sent to the data recipient system 60, for example via the network 70. The integration system configuration module 50 allows for configuration links to external reference systems (for example, a document imaging system). These links allow the user to jump to another system interface from within the system.

The revenue cycle billing system is illustrated by example only. There are other additional types of data processing servers that are used in various industries, including warehouse order fulfillment systems, for example. The host server 30 is configured to receive and store a plurality of data records from multiple user clients 20. These data records are then processed by the quality assurance application server 40 and ultimately released to the data recipient 60. In one embodiment the claims are released to a billing server, for example, for delivery to the data recipient 60 such as a third party payer.

The quality assurance server 40 is configured to analyze each data record to ensure its compliance with the requirements of the particular data recipient 60, for example a third party payer, to which a healthcare claim can ultimately be delivered. The quality assurance application server 40 may work in concert with a quality representative to identify and correct content of data or the format of any individual record. Records that have been processed and validated by the quality assurance application server 40 are updated with the host server 30 via a user client 20. In some embodiments a quality representative station or user interface is included to allow a quality assurance user, for example to facilitate the correction of content of data and format of a patient record for example, where necessary.

A data recipient system 60 can be internal or external, for example in the context of the revenue cycle, a data recipient can be another billing system or an insurance company. Data recipient systems 60, such as a third party payer, receive records from the host server 30.

Figure 3:
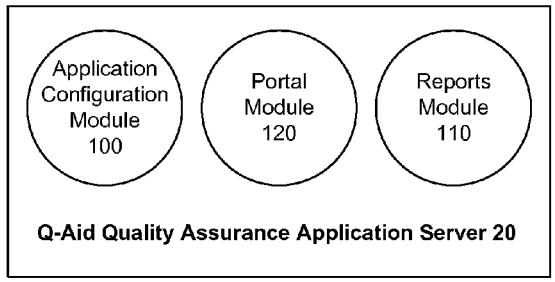
FIG. 3 is a block diagram illustrating an example of a quality assurance application server according to an embodiment of the present invention.

FIG. 3 is a block diagram illustrating an example of a quality assurance application server according to an embodiment of the present invention. In the illustrated embodiment, the quality assurance application server 40 comprises an application configuration module 100, a reports module 110 and a portal module 120.

Figure 4:
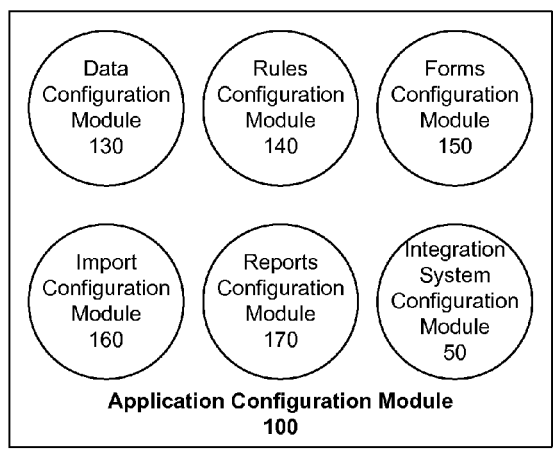
FIG. 4 is a block diagram illustrating an example application configuration module according to an embodiment of the present invention.

FIG. 4 is a block diagram illustrating an example application configuration module according to an embodiment of the present invention. In the illustrated embodiment, the application configuration module 100 comprises a data configuration module 130, a rules configuration module, 140, a forms configuration module 150, import configuration module 160, reports configuration module 170 and an integration system configuration module 50. The rules configuration module 140 covers the entry and maintenance of a rule into a rule set. It supports the creation, testing and implementation of rules, for example record validation rules. A rule can be created or modified by specifying the type of rule and defining the parameters by which the rule can apply. The rules configuration module 140 can additionally be configured to provide for establishing and maintaining error codes and types. In one embodiment, error codes and types are optional for certain rules depending on the particular application to which the error codes and types apply.

Additionally, the rules configuration module 140 can be configured to review and search rules, for example by application, status, date, and other metrics or metadata aspects. The rules may typically be maintained based on requests made by users through the ticket system module 220 which is configured to request and approve new, modified and/or inactivated rules. The rules configuration module 140 can also be configured to run rules reports, rule history and audit reports, and rule activity "hits" reports.

The data configuration module 130 can allow an administrator of the system, for example, to define fields to be captured and reviewed during the quality assurance process. This configuration becomes the basis for other configurations. For example, the fields defined here can be selectable in the Rules configuration when a rule is defined. The forms configuration module 150 allows an administrator, for example, to adjust the placement of the fields within a user interface. Other portions of the user interface may have some customizations that can be made. The reports configuration module 170 can allow reports to be defined and customized for the application. Standard templates or pre-defined reports are available that take advantage of an established business logic, for example healthcare patient encounter business logic. These can then be modified to suit a users needs. The import configuration module 160 defines the interfaces for importing records into the quality assurance system. Each source or interface is defined by a transport method and a location. The data is mapped to the fields defined in the data configuration module 130. The integration system configuration module 50 is a set of tools that can allow links from the quality assurance application server 40 back into the host system or any supporting systems, for example a user interface or a point of service device. The links can be used for retrieving information or placing the user at a point in the host to make changes or update information.

Figure 5:
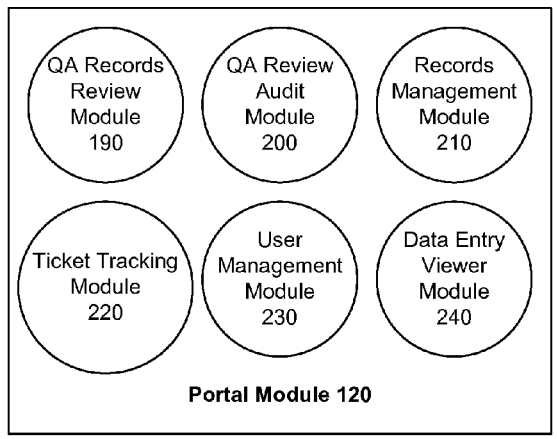
FIG. 5 is a block diagram illustrating an example portal module according to an embodiment of the present invention.

FIG. 5 is a block diagram illustrating an example portal module according to an embodiment of the present invention. In the illustrated embodiment, the portal module 120 comprises data entry viewer module 240, quality assurance records review module 190, a quality assurance review audit module 200, a records management module 210, a user management module 230 and a ticket system module 220. The portal module 120 is configured to provide an interface that serves as an access point to other quality assurance application server modules. The portal module 120 can include a User Interface (UI), that can include the tools that a user can access on a regular basis to perform tasks.

The data entry viewer module 240. This module can be configured to evaluate records as soon as they are received and display the results to the users performing data entry tasks, for example. This facilitates more accurate and timely data collection at the time it is entered into the host system. Data can be gathered from the host through several methods and stored in a database. The rules defined though the rules configuration module 140 is applied to the data. Statistics are accumulated and reports are sent to users that are subscribed to receive those reports. The quality assurance records review module 190 can include the tools that a reviewer can use to evaluate records. In one embodiment the quality assurance records review module 190 can include a main screen that is divided into several sections. The center of the screen may contain a grid which is a spreadsheet style area. Above the grid can include selections for filtering the records displayed in the grid. The right of the filters can include an error display area with action tools above the error display. The reviewers and current record counts can be displayed below the grid. The records displayed on the grid can be limited by selecting specific values for some fields using a records selection filter. The data records can be displayed one per line on the records display grid and the actual fields displayed are configurable. Column headers can be used to sort the records in ascending or descending order, for example. Clicking a record selects that record and displays any errors or flags in the error display area. A reviewer can assign and transfer records to other reviewers or back to an unassigned queue. Also errors are evaluated to determine the exact nature of the problem. A variety of tools can be available inside or outside of the quality assurance application server 40 to obtain information. Links and auto-navigation tools can be used where possible to link to resources and retrieve information. Links to the host system can also be available for correcting data and entering comments via an integration system configuration module 50 illustrated above. Reviewers can add and remove errors as needed to reflect the true status of the record. The quality assurance review audit module 200 encompasses the tools that an auditor can use to validate and track the performance of reviewers. The records management module 210 can control the assignment of records to reviewers. In one embodiment an automatic method is used when records are entered into the system. The logic for determining what records are assigned to reviewers is defined here. In another embodiment a manual method for assigning records is provided to allow a supervisor to manage records and reassign as needed. The ticket system module 220 is similar to a help desk application. Users can request assistance with issues and request changes to the system. Administrative personnel can be able to track requests and communicate with users on the status of those requests. Tasks can be created and assigned to technicians to resolve requests. The user management module 230 can allow a user with sufficient privileges to add or modify user profiles and assign roles to users.

In some embodiments, a ticket system module (220) is configured to support the creation and management of tasks and user requests related to all quality assurance application server modules. For example, the ticket system module (220) may allow the creation and tracking of tickets related to administering the system or operating the system. In one embodiment, a ticket may be created for each claim that is rejected or denied and then the processing of that rejected or denied claim through the revenue cycle process can be managed by way of the ticket and the ticket system module 220.

With respect to administration of the system, tickets may be generated and tracked to ensure timely and accurate completion of tasks including: (a) installing/accessing system; (b) setting-up global system preferences; (c) importing account data from the host system, for example the HIS (healthcare information system) server; (d) adding database/report fields; (e) setting-up/maintaining system tables, for example setting-up/maintaining users and role memberships; and (f) archiving data. In some embodiments, tickets may be generated and tracked to ensure timely and accurate completion of tasks including logging into the system and setting-up user preferences. Additionally, the ticket system module 220 can be configured to manage tickets (for requester and technical support) by: (a) adding a new ticket; (b) append to an existing ticket; (c) filtering ticket list, which can include creating a filter, saving a filter, and applying a filter; (d) reviewing ticket data detail; (e) reviewing ticket data summary; (f) close a ticket; (g) verifying/confirming closed ticket; and (h) reopening a closed ticket.

Additionally, the ticket system module 220 can be configured to manage tickets for technical support, which can include: (a) triaging tickets, which can include assigning a priority and/or target resolution time for the ticket, assigning and transferring tickets; (b) requesting/receiving approval for system change, for example from the client or system owner based on user membership; (c) commenting on a ticket (comment type controlling comment visibility); (d) communicating ticket status/update to requester/distribution group; (e) updating ticket status/priority; and (f) closing a ticket, which can include recording actual resolution time, scoring resolved ticket by technical support team member, and randomly select closed tickets that can receive customer satisfaction survey by email. The ticket system can also be capable of providing rich reporting such as ticket inventory reports, ticket resolution reports, and daily activity reports.

Figure 6:
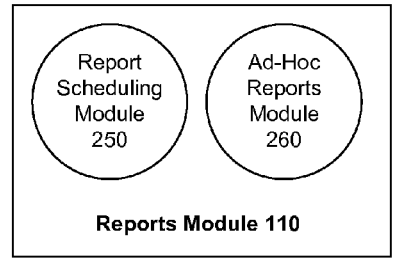
FIG. 6 is a block diagram illustrating an example reports module according to an embodiment of the present invention.

FIG. 6 is a block diagram illustrating an example reports module according to an embodiment of the present invention. In the illustrated embodiment, the reports module 110 comprises a report scheduling module 250 and an ad-hoc reports module 260. The reports module 110 contains the options for viewing, scheduling, and delivering reports to users. The content of the reports is based on the data processed within the quality assurance application platform/system. Reports can be composed of the actual data or statistical data. Reports can be delivered via email or viewed directly and can be created through Ad-hoc reporting. The reports scheduling module 250 can be used to automatically run pre-formatted reports created by the Reports configuration Module 170. Reports can be scheduled to run on particular days and times and the runs can be periodic or event driven. Runtime parameters can be specified and a destination selected. A destination can include the delivery method and a user distribution group. Some of the delivery methods include email, printer, file and viewer. The ad-hoc reports module 260 can allow a user to run a predefined report as needed or create a custom report. The ad-hoc reports module 260 can also specify the destination and other parameters for the instance of the report. If a custom report is selected, the ad-hoc reports module 260 can specify the fields included on the report and report format properties. The reports module 110 is configured to provide an automated and on demand report engine for all of the quality assurance application server modules. Advantageously the reports module 110 can provide automated and ad-hoc reports for administering the system as well as operating the system. For example with respect to administering the system the reports module 110 can provide reports related to: (a) installing and accessing the system for example by users and/or automated processes; (b) setting up global and system and user preferences; (c) importing data from host server or other platforms/systems; (d) adding database/report fields; (e) setting-up/maintaining system tables, for example setting-up/maintaining users and role memberships; (f) archiving data; (g) automated/delivered reports; (h) creating an automated/delivered report, for example, modifying/inactivating/activating an automated/delivered report; (i) setting report recipients/user access; and (j) documenting automated/delivered reports.

Additionally, ad hoc reports can be provided by the reports module 110. For example, the reports module 110 can be configured to receive and manage an ad hoc report request and is also configured to add an ad hoc report request to a user interface menu in one embodiment to facilitate delivering the ad hoc report to users.

With respect to reports on operations of the system, the reports module 110 can be configured to provide reports related to: (a) logging into the system; (b) setting-up user preferences; (c) automated/delivered reports; and (d) requesting access/report receipt. Additionally, the reports module 110 can be configured to: (a) create a user defined on demand report; (b) saving/modifying/inactivating/activating a user defined on demand report; and (c) accessing a standard on demand report in order to provide on demand reports. Furthermore, the reports module 110 can be configured to facilitate requesting an ad hoc report and retrieving and/or receiving a completed ad hoc report. The reports module 110 can also be configured to automatically deliver scheduled reports.

Figure 7A:
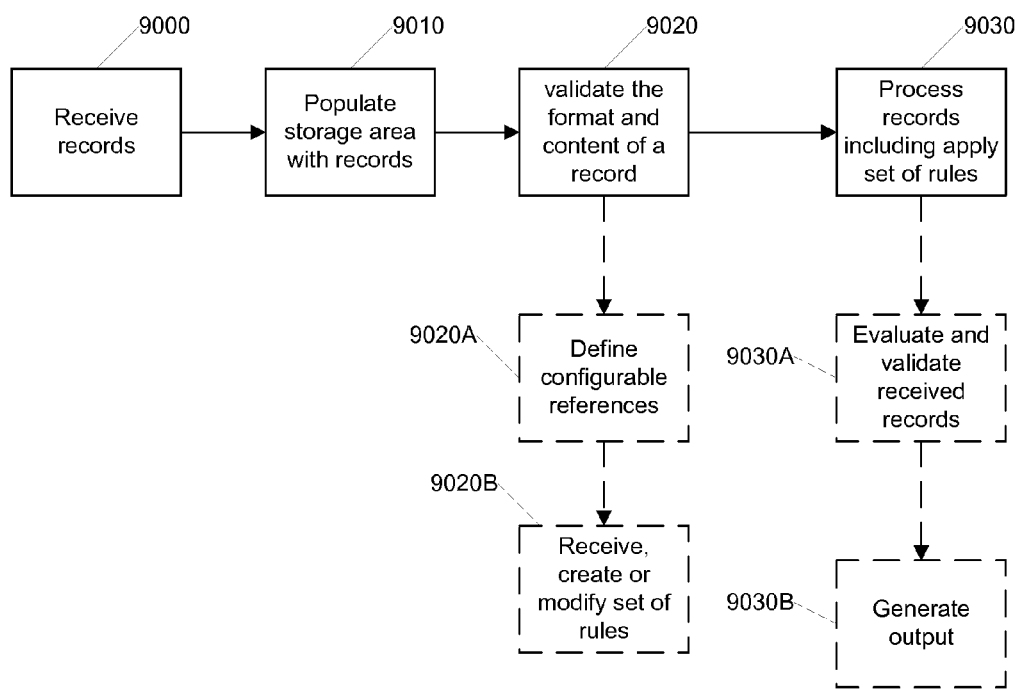
FIG. 7A is a flow diagram illustrating an example process for providing quality assurance in a data processing cycle according to an embodiment of the present invention.

FIG. 7A is a flow diagram illustrating an example process for providing quality assurance in a revenue cycle according to an embodiment of the present invention. The illustrated process can be carried out by the system 10 that was previously described with respect to FIG. 1 and be facilitated by the quality assurance application server 40 that was previously described with respect to FIG. 3. Initially, in step 9000, a first user interface receives records that can be utilized to generate a claim for billing. In one embodiment, the records are received via a user interface such as a computer data network. Next, in step 9010 a storage area is populated with the received records. In one embodiment, each discrete set of record is stored in a separate record in the storage area or database. In step 9020 the quality assurance process can be managed by validating the consistency of the record data. Step 9020 includes sub step 9020A where configurable reference fields to be captured and reviewed during the processing of the records are defined. Also sub step 9020B includes receiving, creating or modifying a set of rules where the configurable reference fields are selectable when the rules are defined. The process then continues to step 9030 where the received records are processed by applying the set of rules to the records. Step 9030 includes sub step 9030B which involves evaluating and validating the received records and generating an output that can be utilized to validate a claim to ensure compliance with a billing standard.

Figure 7B:
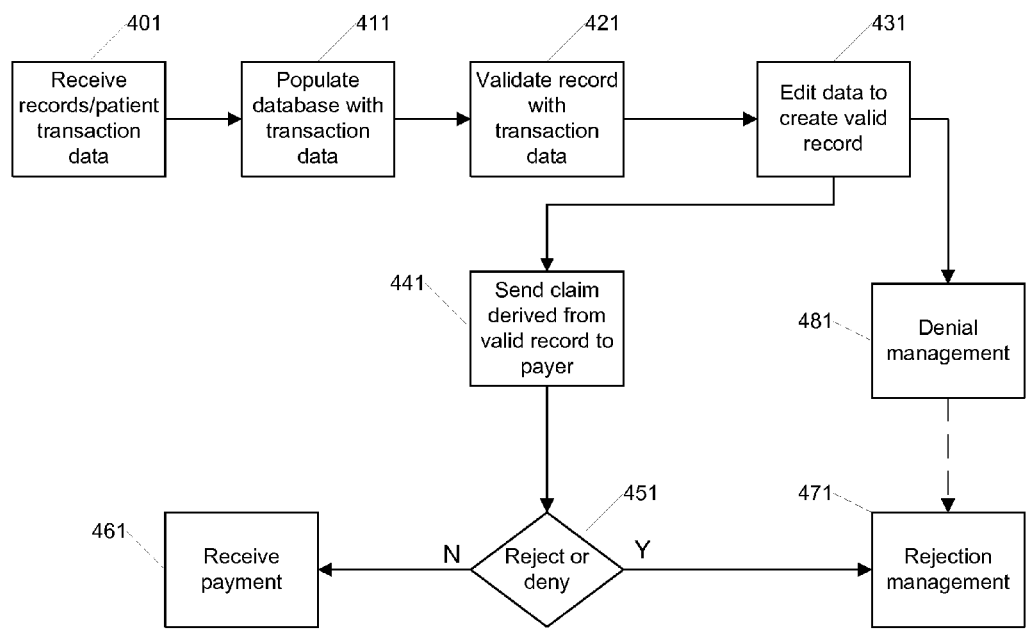
FIG. 7B is a flow diagram illustrating an example method for processing quality assurance records in a data processing cycle according to an embodiment of the present invention.

FIG. 7B is a flow diagram illustrating another example process for providing quality assurance in a revenue cycle according to an embodiment of the present invention. The illustrated process can be carried out by the system 10 that was previously described with respect to FIG. 1 and be facilitated by the quality assurance application server 40 that was previously described with respect to FIG. 3.

Initially, in step 401 the server receives patient transaction data, for example from a point of service device, from a host server, from a user interface or from a service group. In one embodiment, the pos transaction data is received via a computer data network. Next, in step 411 the transaction data is populated into a database, for example on the quality assurance application server 40. In one embodiment, each discrete set of transaction data is stored in a separate record in the database.

After the separate records are created, each record is validated as shown in step 421. This can be done by computer analysis of the data in a record and the format of the record and comparison of the content of the data and the format of the data against the requirements of the third party payer organization. In one embodiment, the rules module 100 coordinates the validation of each record and examines the format of each record and flags any suspect fields for subsequent correction. If the record is shown to be invalid at step 431, in step 441, the record is edited at the host system to create a modified record that is less likely to be rejected or denied by an interested third party. Once the valid record has been created, a claim can be subsequently derived from the record and sent to a third party payer in step 451. This can be done via a network or by more conventional means such as regular post, facsimile and the like. At some point after sending the claim, information about the claim is reviewed to determine (as shown in step 461) if the claim has been rejected or denied. If neither, then in step 471 payment will be received for the claim. If the claim has been rejected or denied, as determined in step 461, then the validation rules should be adjusted so that denial does not occur in the future.

Figure 8:
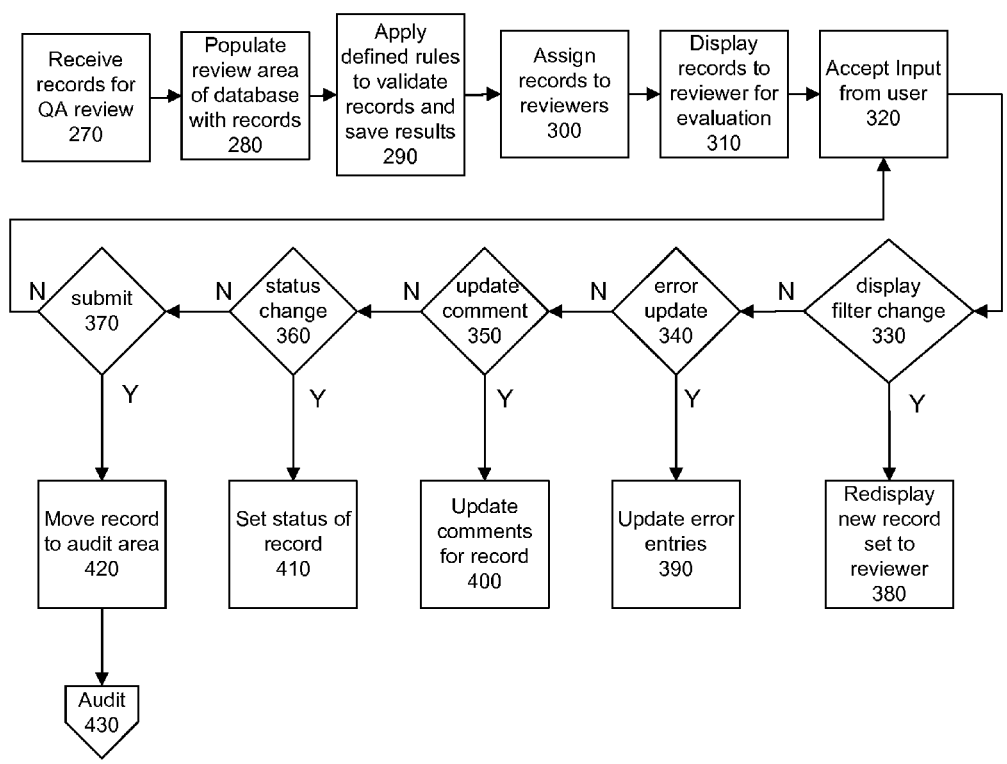
FIG. 8 is a flow diagram illustrating an example process that reviewers use to evaluate the records in the quality assurance records review module.

FIG. 8 is a flow diagram illustrating an example process that reviewers use to evaluate the records in the quality assurance records review module. The illustrated process can be facilitated by the quality assurance records review module 190 that was previously described with respect to FIG. 5. Initially, in step 270 the server receives records for quality assurance review, for example from a point of service device, from a host server, a user interface, or from a service group. In one embodiment, the records received are the patient transaction data received via a computer data network. The process then continues to step 280 where the records are populated into a storage device, for example a database. The database can be associated with a server, for example a host server. In one embodiment, each discrete set of the records is stored in a separate record in the database. After the separate records are created, each record is then validated as shown in step 290. This can be done by computer analysis of the data in a record and the format of the record; a comparison is then made of the content of the data and the format of the data against the requirements of the third party payer organization. In one embodiment, the rules configuration module 140 coordinates the validation of each record and examines the format of each record and flags any suspect fields for subsequent correction. In step 300 the records are assigned to reviewers and in step 310 the records are displayed to the reviewer for evaluation. This step can occur at some point after sending, for example a claim associated with the records to determine if the claim has been rejected or denied. In step 320 an input is received from an interested party, for example a user or subscriber. If a claim, for example, has been rejected or denied due to invalid records associated with the claim, for example, then a rejection management process is initiated and/or a denial management process is initiated to correct any mistakes in the records and then resubmit the claim for remittance. If in step 330 the display filter which allows the records displayed in a grid, for example, to be limited by selecting specific values for some fields has changed, then the process moves to step 380 where a new record set is redisplayed to a reviewer and otherwise, the process continues to step 340. In step 340 it is determined whether or not there is an error update. If there is an error update the error entries are updated in step 390, otherwise the process continues to step 350. In step 350 it is determined whether or not there is a comment update relevant to the records associated with a claim, for example. If a comment update exists the comments are updated for the relevant record in step 400, otherwise the process continues to step 360 where a determination of the status of the record is made. If the status has changed the new status of the record is set in step 410, otherwise the process continues to step 370 where it is determined whether or not to submit the records for audit. If not the process loops back to step 320. If it is decided to submit the records for audit, the process continues to step 420 where the records are moved to the audit area. The process then ends with in the audit area for auditing in step 430.

Figure 9:
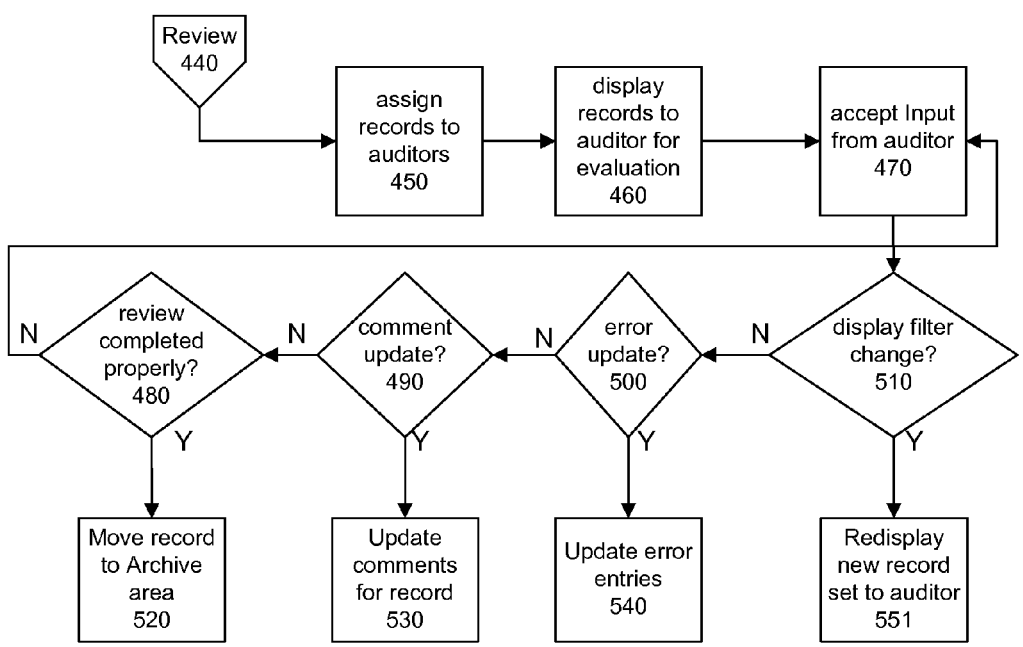
FIG. 9 is a flow diagram illustrating an example auditing process in the quality assurance review audit module.

FIG. 9 is a flow diagram illustrating an example auditing process in the quality assurance review audit module. The illustrated process can be facilitated by the quality assurance audit module 200 that was previously described with respect to FIG. 5. The quality assurance review audit module 200 encompasses the tools that auditors use to validate and track the performance of reviewers. The process starts with step 440 where the records are reviewed and a decision is made to submit the records for audit. The process then continues to step 450 where the records are assigned to auditors. In step 460 the records are displayed to the auditors for evaluation. The process then continues to step 470 where the input from the auditors is accepted. The process then continues to step 510 where it is determined whether or not changes to the display filter occurred. If in step 510 the display filter which allows the records displayed in a grid, for example, to be limited by selecting specific values for some fields has changed, then the process moves to step 551 where a new record set is redisplayed to a reviewer, otherwise the process continues to step 500. In step 500 it is determined whether or not there is an error update. If there is an error update the error entries are updated in step 540, otherwise the process continues to step 490. In step 490 it is determined whether or not there is a comment update relevant to the records. If a comment update exists the comments are updated for the relevant record in step 530, otherwise the process continues to step 480 where a determined if the review was proper or not. If the review was proper the records are moved to an archive area in step 520, otherwise the process loops back to step 470.

Figure 10:
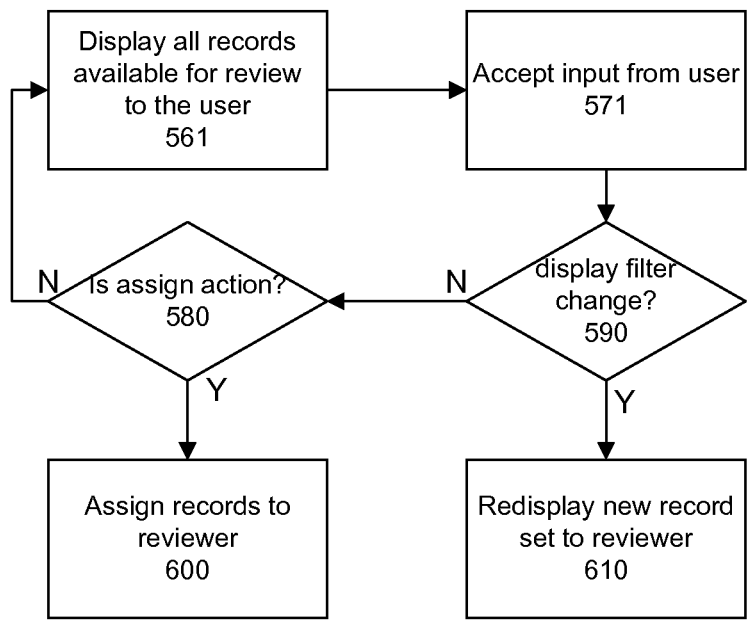
FIG. 10 is a flow diagram illustrating an example of a manual assignment process in the records management module.

FIG. 10 is a flow diagram illustrating an example of a manual assignment process in the records management module. The illustrated process may be facilitated by the records management module 210 that was previously described with respect to FIG. 5. The manual method for assigning records is provided to allow a supervisor to manage records and reassign as needed. Initially, in step 561 all the records available for review are displayed to the user. The process then continues to step 571 where the input from the user is accepted. The process then continues to step 590 where a determination is of whether or not changes to the display filter has occurred. If in step 590 the display filter which allows the records displayed in a grid, for example, to be limited by selecting specific values for some fields has changed, then the process moves to step 610 where a new record set is redisplayed to a reviewer otherwise, the process continues to step 580. In step 580 it is determined whether or not to assign the records to a reviewer. If it is determined to assign the records to a reviewer the records are assigned in step 600, otherwise the process loops back to step 561.

Figure 11:
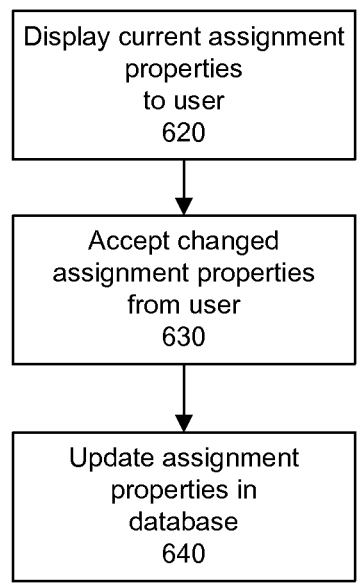
FIG. 11 is a flow diagram illustrating an example of an automatic assignment process in the records management module.

FIG. 11 is a flow diagram illustrating an example of an automatic assignment process in the records management module. The illustrated process can be facilitated by the records management module 210 that was previously described with respect to FIG. 5. The automatic assignment method is used when the records enter the system. The logic for determining what records are assigned to reviewers can be defined in the records management module 210. Initially, in step 620 the current assignment properties are displayed to a user. The process then continues to step 630 where changed assignment properties from the user are accepted. The process concludes with step 640 where the assignment properties are updated in the database.

Figure 12:
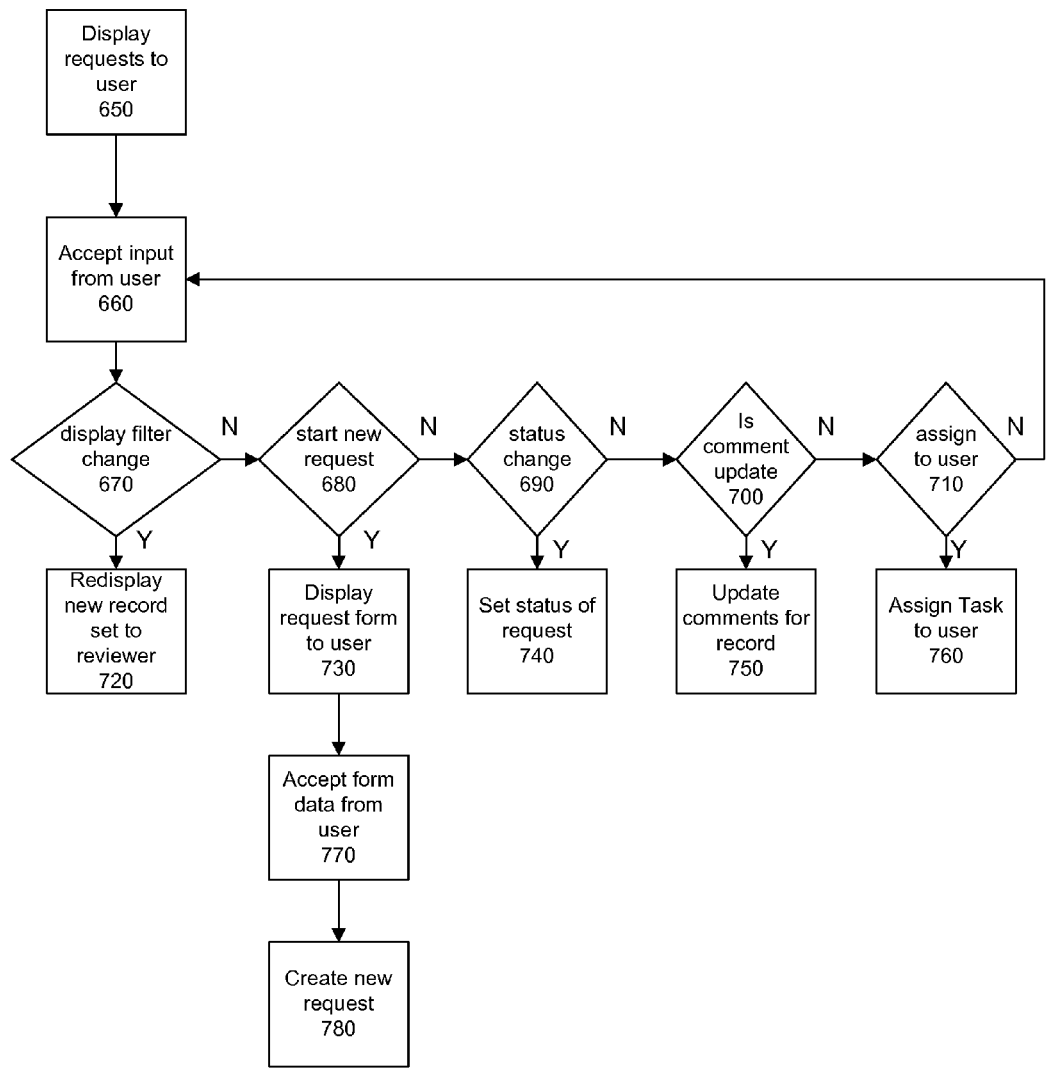
FIG. 12 is a flow diagram illustrating an example process of managing a ticket system request.

FIG. 12 is a flow diagram illustrating an example process of managing a ticket system request. The illustrated process can be facilitated by the portal module 120 that was previously described with respect to FIG. 3. Administrative personnel can review requests and respond to them or assign them to technicians for further review. The ability to add notes and change status can allow administrative personnel to update and close requests. Notification of progress on the request can be sent to the requesting user and other interested users. Some requests can require authorization to proceed. A user with approval authority can approve the actions needed before work can proceed. Upon completion, a summary of actions taken and any related information can be distributed to all interested parties. Initially, in step 650 requests are displayed to a user. Next, in step 660 inputs are accepted from the user and the process continues to step 670 where it is determined whether or not the display filter has changed. If in step 670 the display filter has changed, then the process moves to step 720 where a new record set is redisplayed to the reviewer. Otherwise the process continues to step 680 where it is determined whether or not to start a new user request. If a new request is started the process continues to step 730 where a request form is displayed to the user. In step 770 the data from the user is accepted and in step 780 a new request is created. On the other hand if it is decided not to start a new request the process continues to step 690 where a determination of the status of the record is made. If the status has changed the new status of the record is set in step 740, otherwise the process continues to step 700. In step 700 it is determined whether or not there is a comment update relevant to the records. If a comment update exists the comments are updated for the relevant record in step 750, otherwise the process continues to step 710. In step 710 it is determined whether or not to assign the records or task to a user. If it is determined to assign the records or task to a user the records or task are assigned in step 760, otherwise the process loops back to step 660.

Figure 13:
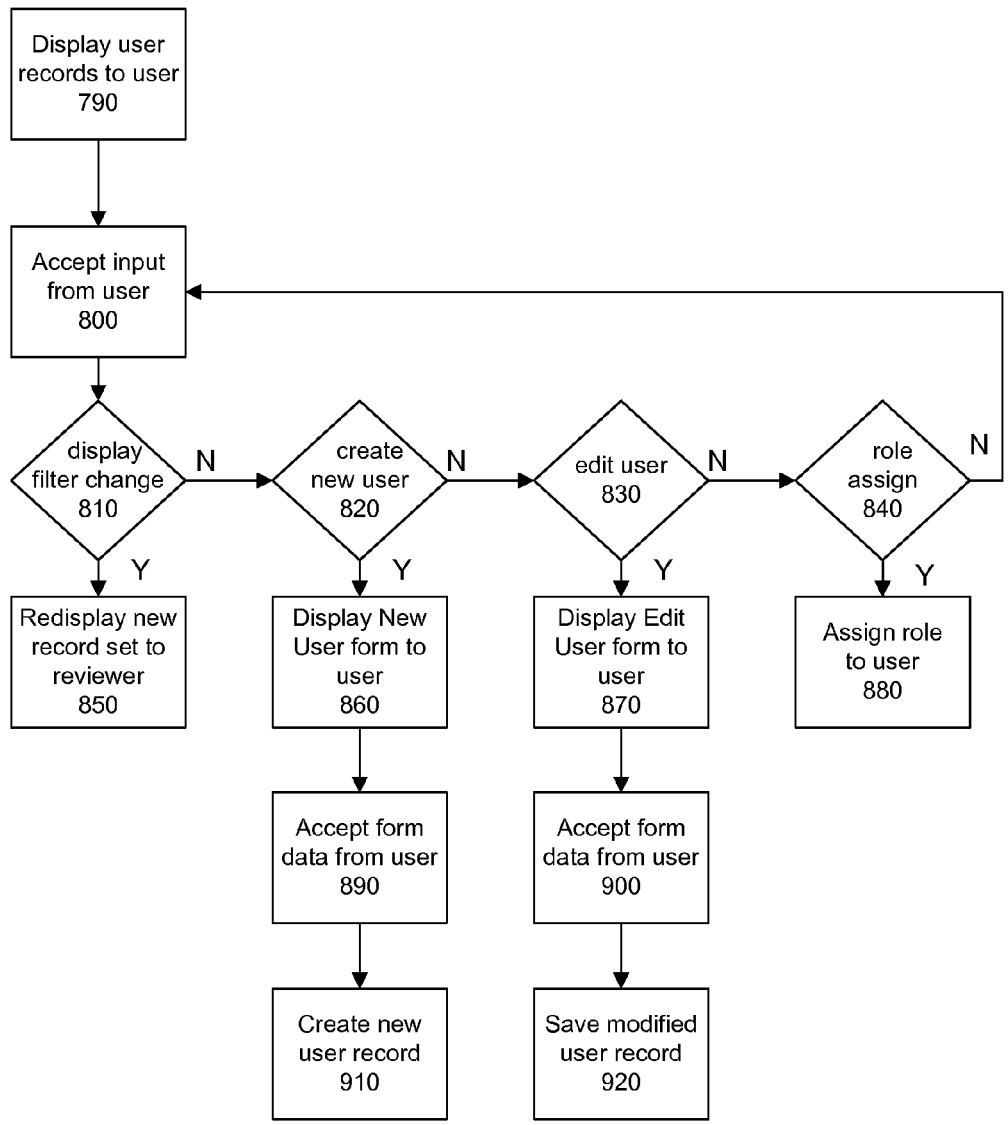
FIG. 13 is a flow diagram illustrating an example of a user management process.

FIG. 13 is a flow diagram illustrating an example of a user management process. The illustrated process can be facilitated by the user management module 230 that was previously described with respect to FIG. 5. The user management module can allow a user with sufficient privileges to add or modify user profiles and assign roles to users. In some embodiments a user can be created and assigned roles, for example distribution groups can be defined and users assigned to them. Initially, in step 790 requests are displayed to a user. Next, in step 800 inputs are accepted from the user and the process continues to step 810 where it is determined whether or not the display filter has changed. If in step 810 the display filter has changed, then the process moves to step 850 where a new record set is redisplayed to the reviewer. Otherwise the process continues to step 820 where it is determined whether or not to create a new user. If a new user is created then the process continues to step 860 where a user form is displayed to the new user. In step 890 the data from the new user is accepted and in step 910 a new user record is created. On the other hand if it is decided not to create a new user the process continues to step 830 where it is determined whether or not to edit a user. If a user is selected for editing then the process continues to step 870 where an edit user form is displayed to the user. In step 900 the data from the user is accepted and in step 920 the modified user record is saved. On the other hand if it is decided that the user will not be edited, the process continues to step 840. In step 840 it is determined whether or not to assign a role or task to the user. If it is determined to assign the role or task to a user in step 880 the role or task are assigned to the user, otherwise the process loops back to step 800.

Figure 14:
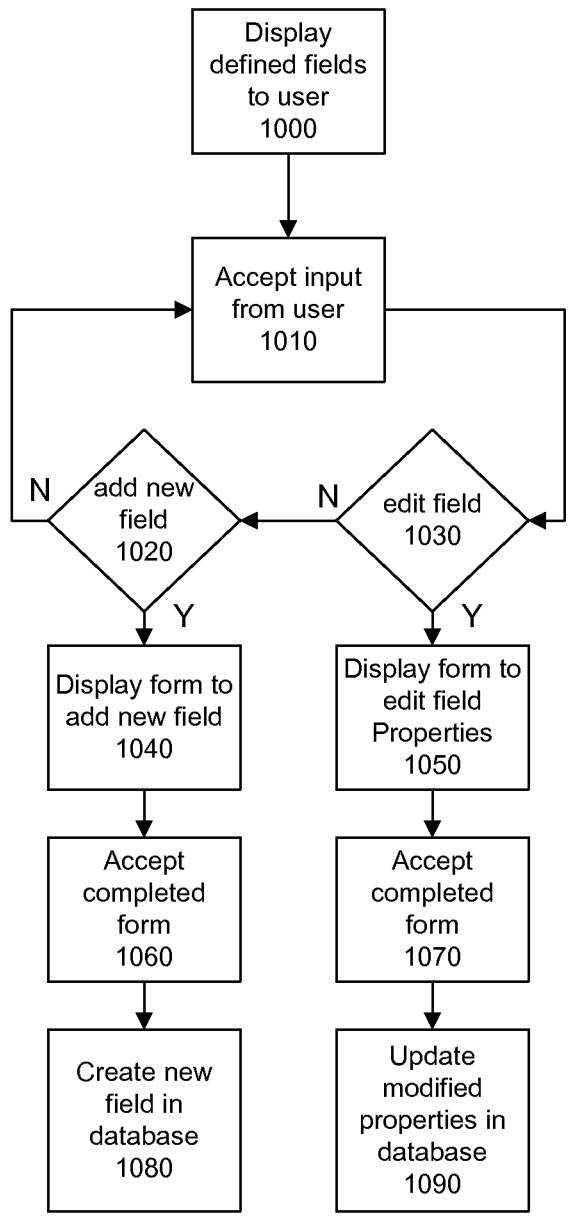
FIG. 14 is a flow diagram illustrating an example process of defining and modifying fields in the data configuration module.

FIG. 14 is a flow diagram illustrating an example process of defining and modifying fields in the data configuration module. The illustrated process can be facilitated by the data configuration module 130 that was previously described with respect to FIG. 4. In one embodiment, the data Configuration module can allow an administrator of the system to define fields of a record to be captured and reviewed during the quality assurance process. This configuration becomes the basis for other configurations. Initially, in step 1000 the defined fields are displayed to a user. The process then continues to step 1010 where inputs from the user are accepted. In step 1030 it is determined whether or not to edit a field. If it is decided to edit a field then the process continues to step 1050 where a form is displayed to facilitate editing the field properties. In step 1070 the completed form is accepted and in step 1090 the database is updated with modified field properties. On the other hand if it is decided not to edit a field the process continues to step 1020 where it is determined whether or not to add a new field. If it is decided to add a new field then the process continues to step 1040 where a form to add new field is displayed to the user. In step 1060 the data/record from the completed form is accepted and in step 1080 a new field is created in the database. On the other hand if it is decided against adding a new field, the process loops back to step 1010.

Figure 15:
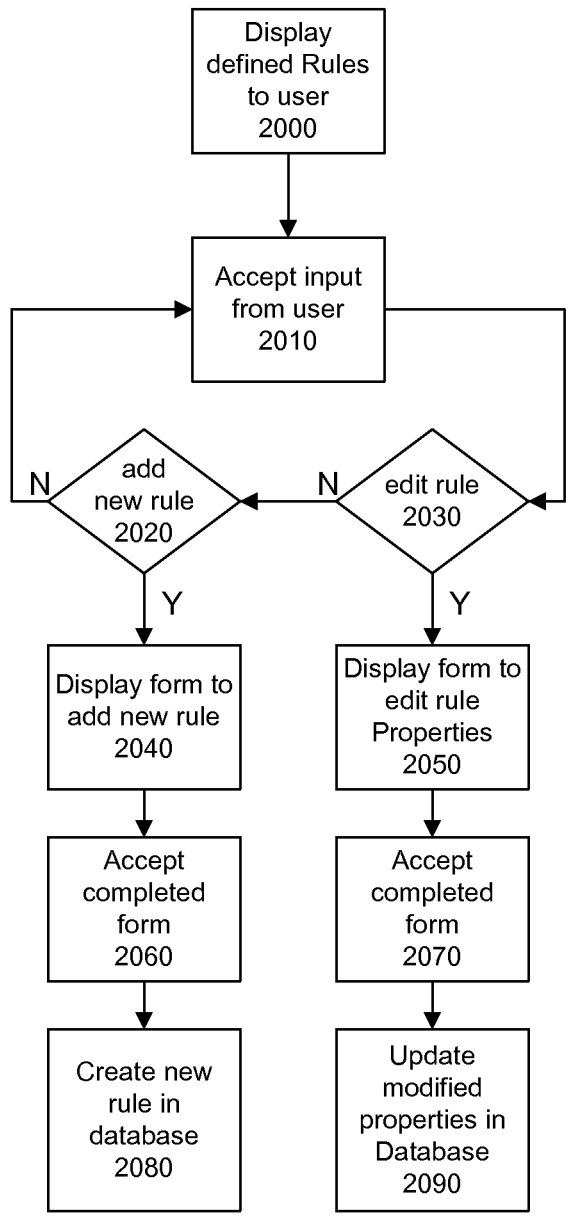
FIG. 15 is a flow diagram illustrating an example process of defining and modifying rules in the rules configuration module.

FIG. 15 is a flow diagram illustrating an example process of defining and modifying rules in the rules configuration module. The illustrated process can be facilitated by the rules configuration module 140 that was previously described with respect to FIG. 4. The rules configuration module 140 can cover the entry and maintenance of a rule into a rules set. A rule can be created or modified by specifying the type of rule and defining the parameters by which the rule can apply. Initially, in step 2000 the defined rules are displayed to a user. The process then continues to step 2010 where inputs from the user are accepted. In step 2030 it is determined whether or not to edit a rule. If it is decided to edit the rule then the process continues to step 2050 where a form is displayed to facilitate editing the rule properties. In step 2070 the completed form is accepted and in step 2090 the database is updated with modified rule properties. On the other hand if it is decided not to edit a rule the process continues to step 2020 where it is determined whether or not to add a new rule. If it is decided to add a new rule then the process continues to step 2040 where a form to add new rule is displayed to the user. In step 2060 the data from the completed form is accepted and in step 2080 a new rule is created in the database. On the other hand if it is decided against adding a new rule, the process loops back to step 2010.

Figure 16:
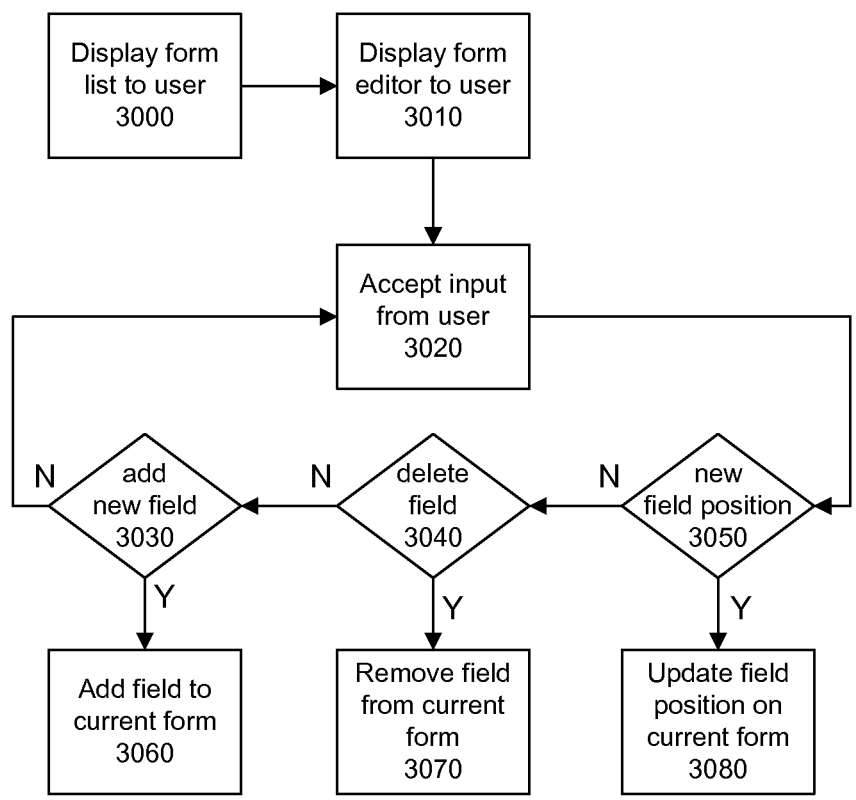
FIG. 16 is a flow diagram illustrating an example process of adding/modifying fields in the forms configuration module.

FIG. 16 is a flow diagram illustrating an example process of adding/modifying a forms configuration module. The illustrated process can be facilitated by the forms configuration module 140 that was previously described with respect to FIG. 4. The forms configuration module 140 allows a user, for example an administrator, to adjust the placement of the fields within a user interface. These fields can be defined in the data configuration module. Initially, in step 3000 the defined rules are displayed in a form list to a user. The process then continues to step 3010 where a form editor is displayed to the user. In step 3020 input from the user is accepted and the process continues to step 3050 where it is determined whether or not a new field position was added. If yes then the process continues to step 3080 where the database is updated with the field position on the current form. On the other hand if no new field position was added the process continues to step 3040 where it is determined whether or not a field has been deleted. If a field has been deleted, the field is removed from the current form in step 3070. On the other hand if no field has been deleted the process continues to step 3030 where it is determined whether or not a new field has been added. If yes the field is added to the current form in step 3060. On the other hand if no new field was added the process loops back to step 3020.

Figure 17:
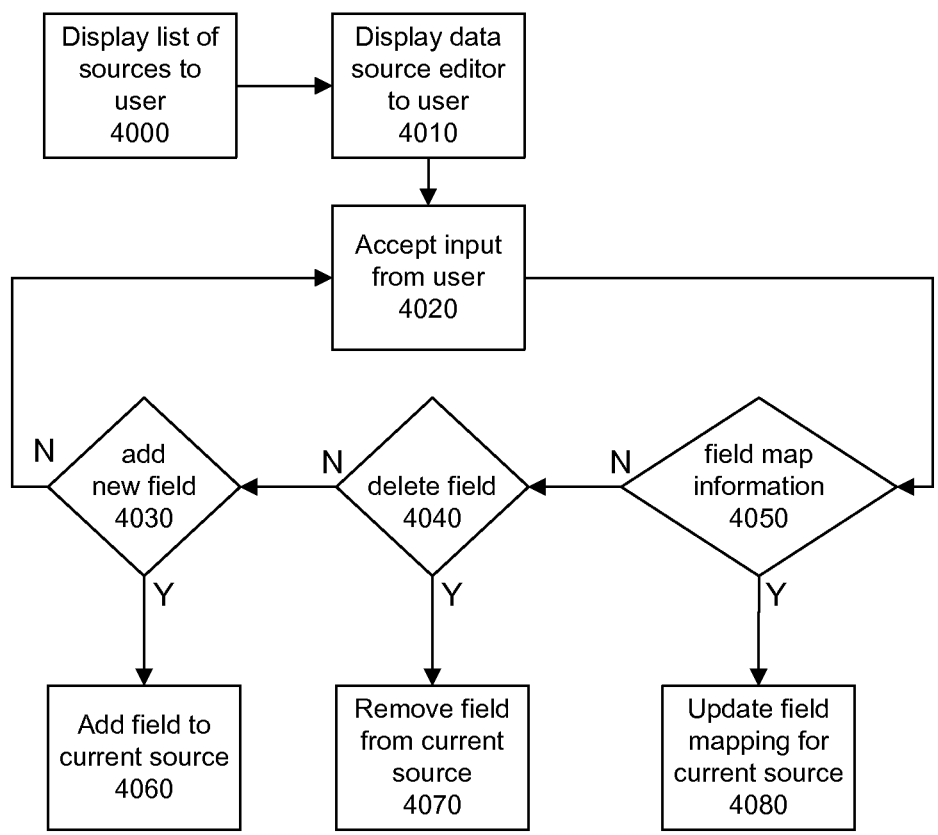
FIG. 17 is a flow diagram illustrating an example process of importing data into the quality assurance application platform/system.

FIG. 17 is a flow diagram illustrating an example process of importing data into the quality assurance application platform/system. The illustrated process can be facilitated by the import data configuration module 160 that was previously described with respect to FIG. 4. The import data configuration module 160 defines the interfaces for importing records into the quality assurance application platform/system. The imported data can be mapped to the fields defined in the data configuration module 130. Initially, in step 4000 the list of sources for importing records is displayed to a user. The process then continues to step 4010 where a source editor is displayed to the user. In step 4020 input from the user is accepted and the process continues to step 4050 where it is determined whether or not field map information exists. If yes then the process continues to step 4080 where the field mapping is updated for the current source. On the other hand if no new field position was added the process continues to step 4040 where it is determined whether or not a field has been deleted. If yes the field is removed from the current source in step 4070. On the other hand if no field has been deleted the process continues to step 4030 where it is determined whether or not a new field has been added. If yes the field is added to the current source in step 4060. On the other hand if no new field was added the process loops back to step 4020.

Figure 18:
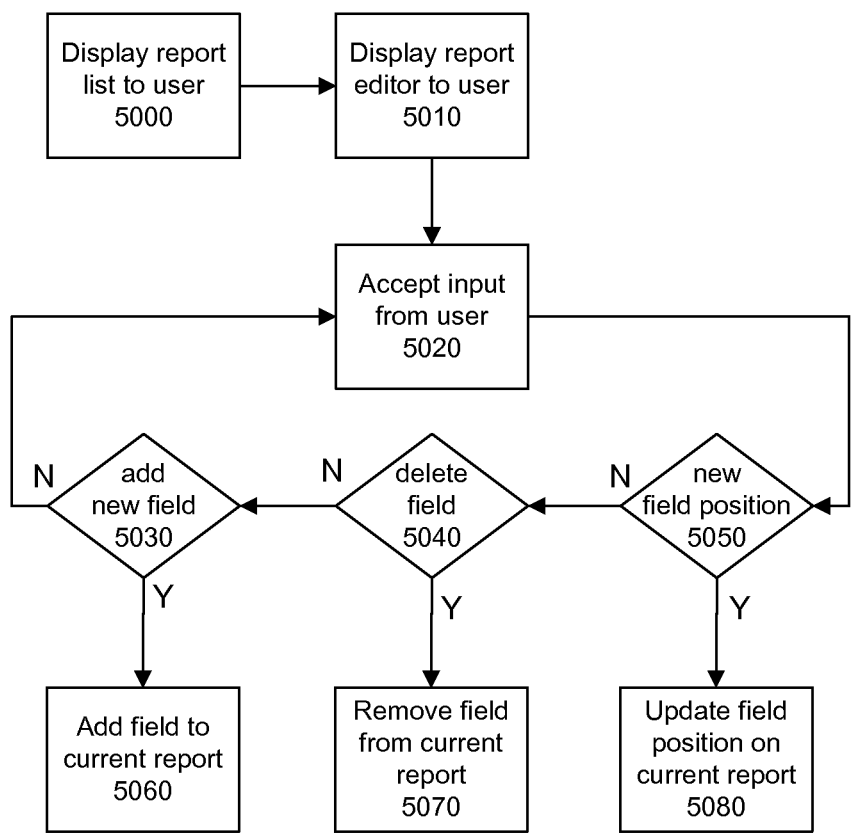
FIG. 18 is a flow diagram illustrating an example process of defining and customizing reports for the quality assurance application platform/system.

FIG. 18 is a flow diagram illustrating an example process of defining and customizing reports for the quality assurance application platform/system. The illustrated process can be facilitated by the reports configuration module 170 that was previously described with respect to FIG. 4. The reports configuration module 170 can allow reports to be defined and customized for the quality assurance application platform/system. In one embodiment standard templates or pre-defined reports are available that take advantage of an existing business logic, for example a healthcare patient encounter business logic. Initially, in step 5000 a report list is displayed to a user. The process then continues to step 5010 where a report editor is displayed to the user. In step 5020 input from the user is accepted and the process continues to step 5050 where it is determined whether or not the field position is new. If yes then the process continues to step 5080 where the field position is updated for the current report. On the other hand if the field position is not new the process continues to step 5040 where it is determined whether or not a field has been deleted. If yes the field is removed from the current report in step 5070. On the other hand if no field has been deleted the process continues to step 5030 where it is determined whether or not a new field has been added. If yes the field is added to the current report in step 5060. On the other hand, if no new field was added, the process loops back to step 5020.

Figure 19:
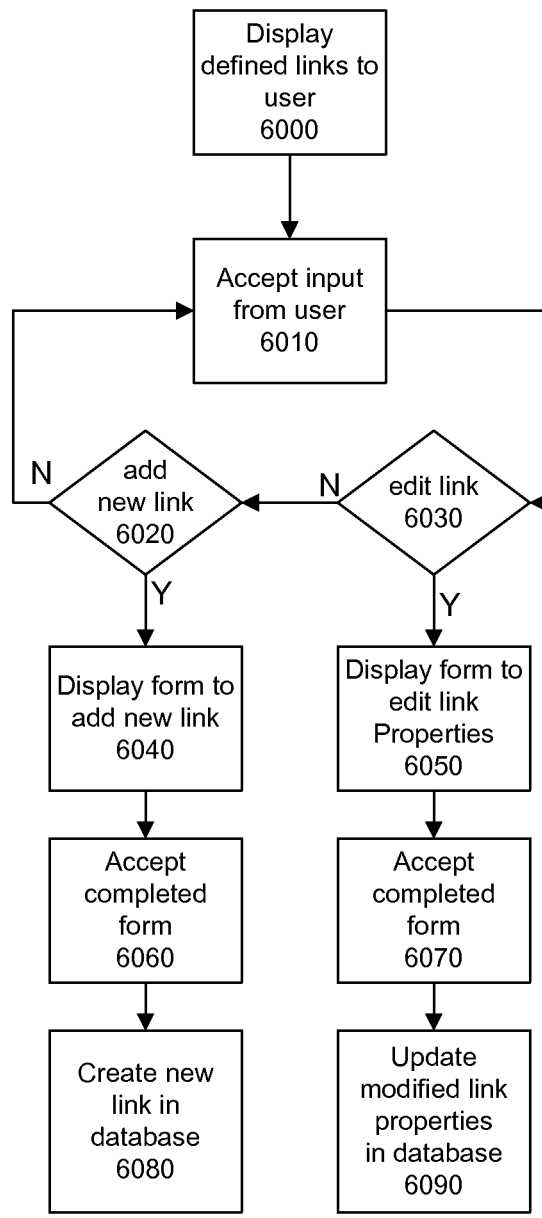
FIG. 19 is a flow diagram illustrating an example process of linking the quality assurance application platform/system with an integrated system.

FIG. 19 is a flow diagram illustrating an example process of integrating the quality assurance application platform/system with an external system. The illustrated process can be facilitated by the integration system configuration module 50 that was previously described with respect to FIG. 4. The integration system configuration module 50 can include a set of tools that allow the links from the quality assurance application platform/system back into an external system, for example the host system or server 30 illustrated in FIG. 1 and any supporting systems. The links can be used for retrieving information or placing the user at a point in the host system to make changes or update information. Initially, in step 6000 the defined links are displayed to a user. The process then continues to step 6010 where inputs from the user are accepted. In step 6030 it is determined whether or not to edit a link. If it is decided to edit a link then the process continues to step 6050 where a form is displayed to facilitate editing the link properties. In step 6070 the completed form is accepted and in step 6090 the database is updated with modified link properties. On the other hand if it is decided not to edit a link the process continues to step 6020 where it is determined whether or not to add a new link. If it is decided to add a new link then the process continues to step 6040 where a form to add new link is displayed to the user. In step 6060 the data from the completed form is accepted and in step 6080 a new link is created in the database. On the other hand if it is decided against adding a new link, the process loops back to step 6010.

Figure 20:
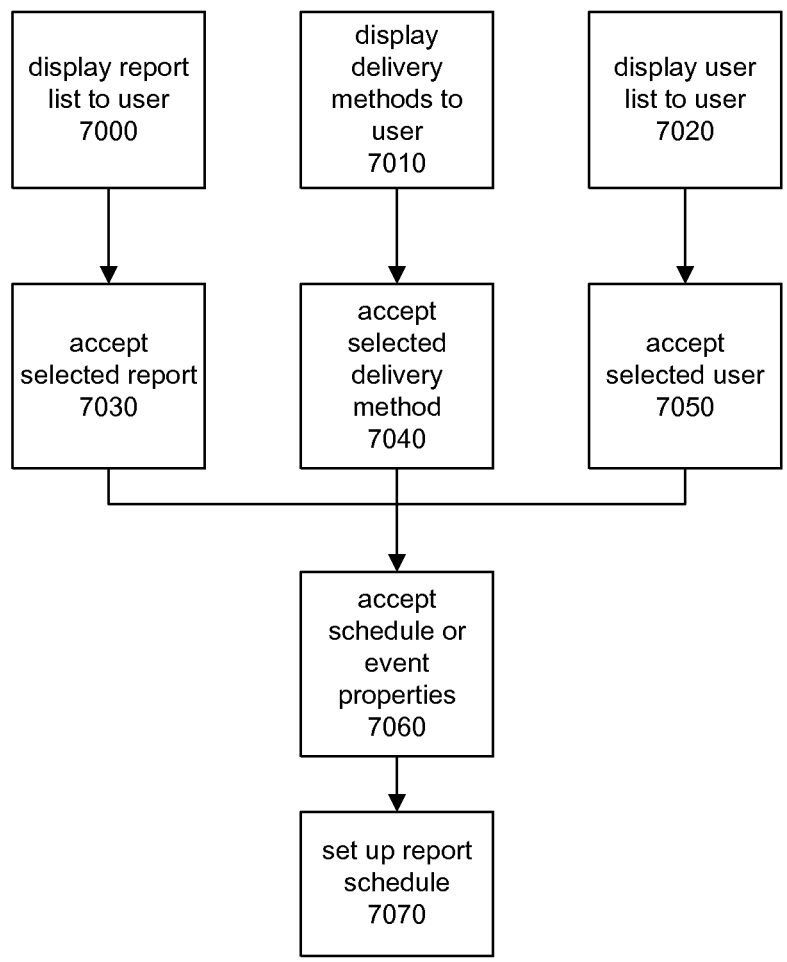
FIG. 20 is a flow diagram illustrating an example process of running a report in the reports module.

FIG. 20 is a flow diagram illustrating an example process of running a report in the reports module. The illustrated process can be facilitated by the reports scheduling module 250 that was previously described with respect to FIG. 6. The report scheduling module 250 can be used to automatically run pre-formatted reports, for example. Reports can be scheduled to run on particular days and times. The runs can be periodic or event driven. Runtime parameters can be specified and a destination selected. A destination can include the delivery method and a user distribution group. Some of the delivery methods include email, printer, file, and viewer. Initially, in step 7000 the report list is displayed to a user. The process then continues to step 7030 where the selected reports are accepted. In step 7060 the schedule or event properties are accepted. The process then continues to step 7070 where the report schedule is setup. In step 7010 a delivery method for the report is displayed to a user. The process then continues to step 7040 where the selected delivery method is accepted. In step 7060 the schedule or event properties are accepted. The process then continues to step 7070 where the report schedule is setup. In step 7020 a user list for the report is displayed to a user. The process then continues to step 7050 where the selected user is accepted. In step 7060 the schedule or event properties are accepted. The process then continues to step 7070 where the report schedule is setup.

Figure 21:
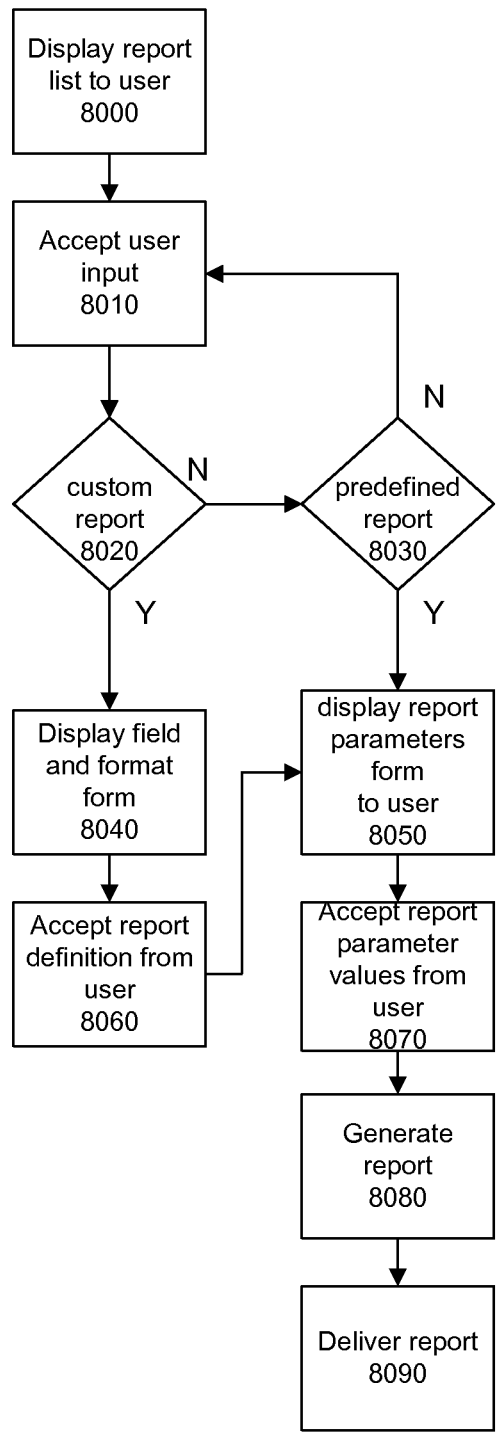
FIG. 21 is a flow diagram illustrating an example ad hoc process of running a report in the reports module.

FIG. 21 is a flow diagram illustrating an example ad hoc process of running a report in the reports module. The illustrated process can be facilitated by the ad-hoc reports module 260 that was previously described with respect to FIG. 6 which is part of the reports module 110 that was previously described with respect to FIG. 3. The ad-hoc reports module 260 can allow a user to run a predefined report as needed or create a custom report. In the process the destination or the report and other parameters for the instance of the report can be specified. If a custom report is selected, the fields included can be specified on the report and the report format properties. Initially, in step 8000 a report list is displayed to a user. The process then continues to step 8010 where inputs from the user are accepted. In step 8020 it is determined whether or not the report is custom. If the report is custom then the process continues to step 8040 where a field and format form is displayed. In step 8060 the report definition from the user is accepted and in step 8050 a report parameters form is displayed to the user. The process then continues to step 8070 where a report parameter value from the user is accepted. In step 8080 a report is generated and in step 8090 the report is delivered. On the other hand if the report is not a custom report the process continues to step 8030 where it is determined whether or not the report is predefined. If the report is predefined the process continues to step 8050 where a report parameters form is displayed to the user. The process then continues to step 8070 where a report parameter value from the user is accepted. In step 8080 a report is generated and in step 8090 the report is delivered. On the other hand if the report is not predefined, the process loops back to step 8010.

Figure 22:
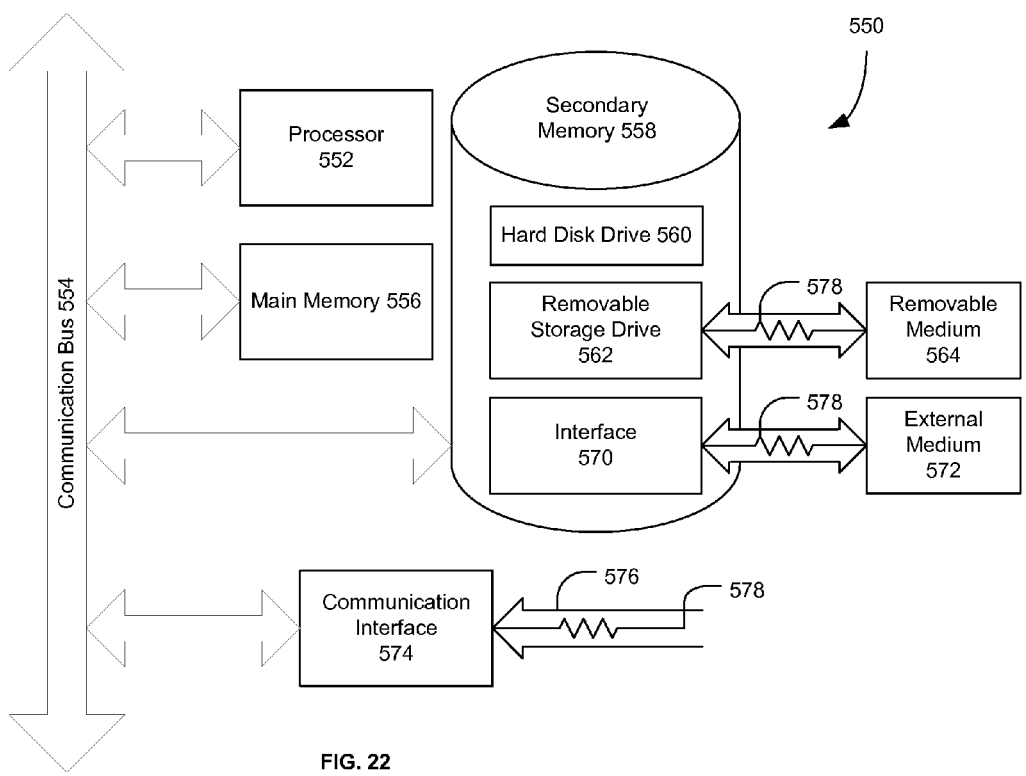
FIG. 22 is a block diagram illustrating an example computer system that may be used in connection with various embodiments described herein.

FIG. 22 is a block diagram illustrating an example computer system 550 that may be used in connection with various embodiments described herein. For example, the computer system 550 may be used in conjunction with a point of service device, quality assurance application server 40, host server, biller station, quality representative station, billing server, or a third party payer server as previously described with respect to FIG. 1. However, other computer systems and/or architectures may be used, as will be clear to those skilled in the art.

The computer system 550 preferably includes one or more processors, such as processor 552. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 552.

The processor 552 is preferably connected to a communication bus 554. The communication bus 554 may include a data channel for facilitating information transfer between storage and other peripheral components of the computer system 550. The communication bus 554 further may provide a set of signals used for communication with the processor 552, including a data bus, address bus, and control bus (not shown). The communication bus 554 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 550 preferably includes a main memory 556 and may also include a secondary memory 558. The main memory 556 provides storage of instructions and data for programs executing on the processor 552. The main memory 556 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 558 may optionally include a hard disk drive 560 and/or a removable storage drive 562, for example a floppy disk drive, a magnetic tape drive, a compact disc ("CD") drive, a digital versatile disc ("DVD") drive, etc. The removable storage drive 562 reads from and/or writes to a removable storage medium 564 in a well-known manner. Removable storage medium 564 may be, for example, a floppy disk, magnetic tape, CD, DVD, etc.

The removable storage medium 564 is preferably a computer readable medium having stored thereon computer executable code (i.e., software) and/or data. The computer software or data stored on the removable storage medium 564 is read into the computer system 550 as electrical communication signals 578.

In alternative embodiments, secondary memory 558 may include other similar means for allowing computer programs or other data or instructions to be loaded into the computer system 550. Such means may include, for example, an external storage medium 572 and an interface 570. Examples of external storage medium 572 may include an external hard disk drive or an external optical drive, or and external magneto-optical drive.

Other examples of secondary memory 558 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 572 and interfaces 570, which allow software and data to be transferred from the removable storage unit 572 to the computer system 550.

Computer system 550 may also include a communication interface 574. The communication interface 574 allows software and data to be transferred between computer system 550 and external devices (e.g. printers), networks, or information sources. For example, computer software or executable code may be transferred to computer system 550 from a network server via communication interface 574. Examples of communication interface 574 include a modem, a network interface card ("NIC"), a communications port, a PCMCIA slot and card, an infrared interface, and an IEEE 1394 fire-wire, just to name a few.

Communication interface 574 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 574 are generally in the form of electrical communication signals 578. These signals 578 are preferably provided to communication interface 574 via a communication channel 576. Communication channel 576 carries signals 578 and can be implemented using a variety of wired or wireless communication means including wire or cable, fiber optics, conventional phone line, cellular phone link, wireless data communication link, radio frequency (RF) link, or infrared link, just to name a few.

Computer executable code (i.e., computer programs or software) is stored in the main memory 556 and/or the secondary memory 558. Computer programs can also be received via communication interface 574 and stored in the main memory 556 and/or the secondary memory 558. Such computer programs, when executed, enable the computer system 550 to perform the various functions of the present invention as previously described.

In this description, the term "computer readable medium" is used to refer to any media used to provide computer executable code (e.g., software and computer programs) to the computer system 550. Examples of these media include main memory 556, secondary memory 558 (including hard disk drive 560, removable storage medium 564, and external storage medium 572), and any peripheral device communicatively coupled with communication interface 574 (including a network information server or other network device). These computer readable mediums are means for providing executable code, programming instructions, and software to the computer system 550.

In an embodiment that is implemented using software, the software may be stored on a computer readable medium and loaded into computer system 550 by way of removable storage drive 562, interface 570, or communication interface 574. In such an embodiment, the software is loaded into the computer system 550 in the form of electrical communication signals 578. The software, when executed by the processor 552, preferably causes the processor 552 to perform the inventive features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

Furthermore, those of skill in the art will appreciate that the various illustrative logical blocks, modules, circuits, and method steps described in connection with the above described figures and the embodiments disclosed herein can often be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block, circuit or step is for ease of description. Specific functions or steps can be moved from one module, block or circuit to another without departing from the invention.

Moreover, the various illustrative logical blocks, modules, and methods described in connection with the embodiments disclosed herein can be implemented or performed with a general purpose processor, a digital signal processor ("DSP"), an ASIC, FPGA or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

The invention claimed is:

1. A health care billing quality assurance application system comprising:
    a non-transitory computer readable storage device configured to store executable programmed modules;

at least one processor communicatively coupled with the non-transitory computer readable storage device configured to execute programmed modules stored therein; and one or more executable software modules that, when executed by the at least one processor, receives a first patient data record comprising a field that identifies a first payer, wherein the first patient data record is to be used to generate a first claim to be submitted to the first payer, maps data in the first patient data record to one or more fields, applies a first set of rules determined by the first payer to the one or more fields comprising first patient data record data to determine whether the first patient data record is potentially noncompliant with a standard of the first payer, and if the first patient data record is potentially noncompliant with the standard of the first payer, flags any suspect ones of the one or more fields comprising first patient data record data, and assigns the first patient data record to at least one of a plurality of reviewers for quality assurance review prior to generating and submitting the first claim to the first payer; and receives a second patient data record, different from the first patient data record, comprising a field that identifies a second payer, wherein the second patient data record is to be used to generate a second claim to be submitted to the second payer, maps data in the second patient data record to one or more fields, applies a second set of rules determined by the second payer to the one or more fields comprising second patient data record data to determine whether the second patient data record is potentially noncompliant with a standard of the second payer, wherein the standard of the second payer is different from the standard of the first payer, and if the second patient data record is potentially noncompliant with the standard of the second payer, flags any suspect ones of the one or more fields comprising second patient data record data, and assigns the second patient data record to at least one of a plurality of reviewers for quality assurance review prior to generating and submitting the second claim to the second payer.

2. The quality assurance application system of claim 1, wherein the one or more executable software modules generates the first claim from the first patient data record and submits the first claim to the first payer.

3. The quality assurance application system of claim 2, wherein the one or more executable software modules determines if the first claim has been rejected by the first payer.

4. The quality assurance application system of claim 1, wherein the standard of the first payer is set manually by an interested party.

5. The quality assurance application system of claim 1, further comprising a forms configuration module configured to allow adjustment of the one or more fields comprising first patient data record data and the one or more fields comprising second patient data record data within a user interface.

6. The quality assurance application system of claim 1, wherein the one or more executable software modules further provide a customizable user interface for receiving the first and second patient data records.

7. The quality assurance application system of claim 1, wherein the one or more executable software modules further generate a report.

8. The quality assurance application system of claim 7, wherein the report is based on a pre-defined template.

9. The quality assurance application system of claim 7, wherein the report is a customized report.

10. The system of claim 1, wherein the payer is an insurance company.

11. The system of claim 1, further comprising a forms configuration module configured to allow adjustment of the one or more fields within a user interface.

12. A health care billing quality assurance application review method comprising, by at least one hardware processor:

receiving a first patient data record comprising a field that identifies a first payer, wherein the first patient data record is to be used to generate a first claim to be submitted to the first payer;

populating a storage area with the first patient data record;

mapping data in the first patient data record to one or more fields;

applying a set of rules determined by the first payer to the one or more fields comprising first patient data record data to determine whether the first patient data record is potentially noncompliant with a standard of the first payer, and if the first patient data record is potentially noncompliant with the standard of the first payer, flagging any suspect ones of the one or more fields comprising first patient data record data, and assigning the first patient data record to at least one of a plurality of reviewers for quality assurance review prior to generating and submitting the first claim to the first payer; and receiving a second patient data record, different from the first patient data record, comprising a field that identifies a second payer, wherein the second patient data record is to be used to generate a second claim to be submitted to the second payer;

populating a storage area with the second patient data record;

mapping data in the second patient data record to one or more fields;

applying a set of rules determined by the second payer to the one or more fields comprising second patient data record data to determine whether the second patient data record is potentially noncompliant with a standard of the second payer, and if the second patient data record is potentially noncompliant with the standard of the second payer, flagging any suspect ones of the one or more fields comprising second patient data record data, and assigning the second patient data record to at least one of a plurality of reviewers for quality assurance review prior to generating and submitting the second claim to the second payer.

13. The method of claim 12, further comprising submitting one of the first or second patient data records for auditing.

14. The method of claim 12, further comprising, if the first patient data record is potentially noncompliant with the standard of the first payer, displaying the one or more fields for review by the at least one of the plurality of reviewers and receiving input from the at least one of the plurality of reviewers.

15. The method of claim 12, further comprising if the first patient data record is potentially noncompliant with the standard of the first payer:
- receiving a modification of the first patient data record; and
- sending the modified first patient data record to the first payer for remittance.

16. The method of claim 12, further comprising:
- determining that the first patient data record is potentially noncompliant with the standard of the first payer;
- automatically selecting a first reviewer from the plurality of reviewers;
- assigning the first patient data record to the first reviewer for quality assurance review;
- determining that the second patient data record is potentially noncompliant with the standard of the second payer;
- automatically selecting a second reviewer from the plurality of reviewers, wherein the second reviewer is different than the first reviewer; and
- assigning the second patient data record to the second reviewer for quality assurance review.

17. A non-transitory computer readable medium having stored thereon one or more sequences of instructions for causing one or more processors to perform steps comprising:
- receiving a first patient data record comprising a field that identifies a first payer, wherein the first patient data record is to be used to generate a first claim to be submitted to the first payer;
- populating a storage area with the first patient data record;
- mapping data in the first patient data record to one or more fields;
- applying a set of rules determined by the first payer to the one or more fields comprising first patient data record data to determine whether the first patient data record is potentially noncompliant with a standard of the first payer, and
- if the first patient data record is potentially noncompliant with the standard of the first payer,
  - flagging any suspect ones of the one or more fields comprising first patient data record data, and
  - assigning the first patient data record to at least one of a plurality of reviewers for quality assurance review prior to generating and submitting the first claim to the first payer; and
- receiving a second patient data record, different from the first patient data record, comprising a field that identifies a second payer, wherein the second patient data record is to be used to generate a second claim to be submitted to the second payer;
- populating a storage area with the second patient data record;
- mapping data in the second patient data record to one or more fields;
- applying a set of rules determined by the second payer to the one or more fields comprising second patient data record data to determine whether the second patient data record is potentially noncompliant with a standard of the second payer, and
- if the second patient data record is potentially noncompliant with the standard of the second payer,
  - flagging any suspect ones of the one or more fields comprising second patient data record data, and
  - assigning the second patient data record to at least one of a plurality of reviewers for quality assurance review prior to generating and submitting the second claim to the second payer.

18. The medium of claim 17, wherein the steps further comprise submitting one of the first or second patient data records for auditing.

19. The medium of claim 17, wherein the steps further comprise, if the first patient data record is potentially noncompliant with the standard of the first payer, displaying the one or more fields for review by the at least one of the plurality of reviewers and receiving input from the at least one of the plurality of reviewers.

20. The medium of claim 17, wherein the steps further comprise, if the first patient data record is potentially noncompliant with the standard of the first payer:
- receiving a modification of the first patient data record; and
- sending the modified first patient data record to the first payer for remittance.

21. The medium of claim 17, wherein the steps further comprise:
- determining that the first patient data record is potentially noncompliant with the standard of the first payer;
- automatically selecting a first reviewer from the plurality of reviewers;
- assigning the first patient data record to the first reviewer for quality assurance review;
- determining that the second patient data record is potentially noncompliant with the standard of the second payer;
- automatically selecting a second reviewer from the plurality of reviewers, wherein the second reviewer is different than the first reviewer; and
- assigning the second patient data record to the second reviewer for quality assurance review.

22. The medium of claim 17, wherein the steps further comprise generating the first claim from the first patient data record and submitting the first claim to the first payer.

23. The medium of claim 22, wherein the steps further comprise determining if the first claim has been rejected by the first payer.

24. The medium of claim 17, wherein the steps further comprise providing a user interface for adjusting one or more fields.

25. The medium of claim 24, wherein the steps further comprise providing a user interface for adjusting one or more fields comprising first patient data record data and one or more fields comprising second patient data record data.

26. The medium of claim 17, wherein the steps further comprise providing a customizable user interface for receiving the first and second patient data records.

27. The medium of claim 17, wherein the steps further comprise generating a report.

28. The medium of claim 27, wherein the steps further comprise generating a report based on a pre-defined template.

29. The medium of claim 28, wherein the steps further comprise generating a customized report based on a pre-defined template.

* * * * *